(12) United States Patent
Jackson et al.

(10) Patent No.: US 7,053,147 B2
(45) Date of Patent: May 30, 2006

(54) PRODUCTION OF UNSATURATED ACIDS OR ESTERS THEREOF

(75) Inventors: Samuel David Jackson, Durham (GB); David William Johnson, North Yorkshire (GB); John David Scott, Cheshire (GB); Gordon James Kelly, Durham (GB); Brian Peter Williams, Lancashire (GB)

(73) Assignee: Lucite International UK Limited (GB)

( * ) Notice: Subject to any disclaimer, the term of this patent is extended or adjusted under 35 U.S.C. 154(b) by 190 days.

(21) Appl. No.: 10/346,191

(22) Filed: Jan. 17, 2003

(65) Prior Publication Data

US 2003/0233012 A1 Dec. 18, 2003

Related U.S. Application Data

(62) Division of application No. 09/647,876, filed as application No. PCT/GB99/01029 on Apr. 1, 1999, now Pat. No. 6,544,924.

(30) Foreign Application Priority Data

Apr. 8, 1998 (GB) .................................. 9807498.2

(51) Int. Cl.
*C08L 33/12* (2006.01)

(52) U.S. Cl. .................................................... 524/560

(58) Field of Classification Search ................ 524/560, 524/561, 562; 502/242, 243, 251

See application file for complete search history.

(56) References Cited

U.S. PATENT DOCUMENTS

| 3,933,888 A | 1/1976 | Schlaefer |
| 4,837,193 A | 6/1989 | Akizuki et al. |
| 4,845,070 A | 7/1989 | Montag |
| 4,990,662 A | 2/1991 | Hagen et al. |
| 5,077,256 A | 12/1991 | Yamamoto et al. |
| 5,187,132 A | 2/1993 | Zones et al. |
| 5,258,346 A | 11/1993 | Huang et al. |

FOREIGN PATENT DOCUMENTS

| EP | 138 295 | 4/1985 |
| EP | 0227461 | 7/1987 |

OTHER PUBLICATIONS

Yoo, J.S., "Silica supported metal-doped cesium ion catalyst for methacrylic acid synthesis via condensation of propionic acid with formaldehyde," Applied Catalysis A: General, 1993, 102, pp. 215-232.

*Primary Examiner*—Edward M. Johnson
(74) *Attorney, Agent, or Firm*—Mayer, Brown, Rowe & Maw LLP

(57) ABSTRACT

The production of ethylenically unsaturated acids or esters by the catalytic reaction of an alkanoic acid or ester, especially methyl propionate, with formaldehyde, and a catalyst therefor wherein the catalyst comprises a porous high surface area silica containing 1–10% by weight of an alkali metal, especially cesium (expressed as a metal) and having compounds of at least one modifier element selected from boron, magnesium, aluminium, zirconium and hafnium dispersed in the pores of said silica in such amount that the catalyst contains a total of 0.25 to 2 gram atoms of primary modifier element per 100 moles of silica.

10 Claims, No Drawings

PRODUCTION OF UNSATURATED ACIDS OR ESTERS THEREOF

CROSS REFERENCE TO RELATED APPLICATIONS

This application is a divisional of U.S. Ser. No. 09/647,876, filed Dec. 1, 2000 now U.S. Pat. No. 6,544,924, which claims benefit of International Application No. PCT/GB99/01029, filed Apr. 1, 1999. These applications in their entirety are incorporated herein by reference.

This invention relates to the production of ethylenically unsaturated acids or esters thereof, particularly methacrylic acid or alkyl methacrylates, and in particular to novel catalysts therefor.

Such acids or esters may be made by reacting an alkanoic acid (or ester) of the formula R'—CH$_2$—COOR, where R and R' are each, independently, hydrogen or an alkyl group especially a lower alkyl group containing for example 1–4 carbon atoms, with formaldehyde. Thus methacrylic acid or alkyl esters thereof, especially methyl methacrylate, may be made by the catalytic reaction of propionic acid, or the corresponding alkyl ester, e.g. methyl propionate, with formaldehyde in accordance with the reaction sequence:

The reaction is typically effected at an elevated temperature, usually in the range 250–400° C., using a basic catalyst. Where the desired product is an ester, the reaction is preferably effected in the presence of the relevant alcohol in order to minimise the formation of the corresponding acid through hydrolysis of the ester. Also for convenience it is often desirable to introduce the formaldehyde in the form of formalin. Hence for the production of methyl methacrylate, the reaction mixture fed to the catalyst will generally consist of methyl propionate. methanol, formaldehyde and water.

Suitable catalysts that have been used include alkali metal-doped, especially cesium-doped, silica catalysts. It has been found that certain cesium-doped silica catalysts, i.e. those based upon gel silicas have an unacceptable service life as they lose their activity and selectivity in a relatively short time. This activity loss may be attributed to two factors.

Firstly, the alkali metal compound employed may exhibit appreciable volatility under the reaction conditions employed and so there may be a loss of activity through loss of alkali metal. As described in U.S. Pat. No. 4,990,662, this may be overcome by incorporating a suitable alkali metal compound into the process gas stream so that alkali metal compound is deposited on the catalyst during operation to compensate for any alkali metal compound lost through volatilisation.

Secondly, as may be inferred from U.S. Pat. No. 4,942,258, it is believed that for the alkali metal to be active, the support should have a certain minimum surface area. The requisite area is dependent on the amount of alkali metal in the catalyst: thus it may be inferred that there is a minimum surface area required per unit of alkali metal. During operation, there is a tendency for the silica support to lose surface area. Thus under the reaction conditions there is a risk of hydrolysis of the silica, not only by the water produced by the reaction, but also from water present in the reaction mixture, for example resulting from introduction of the formaldehyde as formalin. We have found that the loss of performance of the gel silica catalysts with time largely results from such hydrolysis causing a decrease in the surface area of the catalyst with time.

Typically the catalyst contains 1–10% by weight of the alkali metal. Preferably at least 2% by weight of alkali metal is employed so that the process can be operated at sufficiently low temperatures that loss of alkali metal through volatilisation can be minimised. The operation at low temperatures has the additional advantage that the rate of deposition of coke, which tends to block the pores of the silica and so reduce activity, is decreased.

We have found that the incorporation of certain modifiers, such as compounds of elements such as boron, aluminium, magnesium, zirconium, or hafnium into the catalysts, in addition to the alkali metal, retards the rate of surface area decrease. In the catalysts of the invention, it is important that the modifier is intimately dispersed in the silica, rather than simply being in the form of particles mixed with the silica particles. It is probable that the metal compounds in whatever form they are added will convert to oxides or (particularly at the surface of the silica) hydroxides before or during drying, calcination or operation of the catalyst and interact either on the surface or in the bulk of the silica structure in that form. Furthermore, it is important that the amount of modifier is within certain limits: if there is too little modifier, no significant advantage accrues while if too much modifier is employed the selectivity of the catalyst may be adversely affected. Generally the amount of modifier required is in the range 0.25 to 2 gram atoms of the modifier element per 100 moles of silica.

The aforesaid U.S. Pat. No. 4,990,662 indicates that silicas may contain materials such as aluminium, zirconium, titanium, and iron compounds as trace impurities. That reference however indicates that improved catalysts are obtained if such impurities are removed by acid extraction to give a trace impurity content below 100 ppm.

EP 0 265 964 discloses the use of silica supported catalysts containing antimony as well as the alkali metal. The description indicates that the alumina content is desirably less than 500 ppm. A comparative, antimony-free, example discloses the use of a composition containing 950 ppm alumina. This corresponds to 0.11 gram atoms of aluminium per 100 moles of silica.

U.S. Pat. No. 3,933,888 discloses the production of methyl methacrylate by the above reaction using a catalyst formed by calcining a pyrogenic silica with a base such as a cesium compound, and indicates that the pyrogenic silica may be mixed with 1–10% by weight of pyrogenic zirconia. That reference also discloses the use of a catalyst made from a composition containing cesium as the alkali metal and a small amount of borax. The amount of boron however is about 0.04 gram atoms per 100 moles of silica and so is too small to have any significant stabilising effect.

DE 2349054 C, which is nominally equivalent to U.S. Pat. No. 3,933,888, exemplifies catalysts containing zirconia or hafnia in admixture with the silica: the results quoted indicate that the zirconia or hafnia containing catalysts give a lower yield based upon the amount of formaldehyde employed.

Yoo discloses In "Applied Catalysis", 102, (1993) pages 215–232 catalysts of cesium supported on silica doped with various modifiers. While bismuth appeared to be a satisfactory dopant, catalysts doped with lanthanum, lead or thallium gave short term improvements. However high levels of lanthanum gave products of low selectivity while low levels of lanthanum gave catalysts that sintered much faster than the bismuth doped catalysts. The effective additives were all highly toxic heavy metals with appreciable volatility: these considerations preclude their use as catalyst components.

The aforementioned U.S. Pat. No. 3,933,888 indicated that it was important to use a pyrogenic silica and showed that other types of silicas were unsuitable. The pyrogenic silicas said to be suitable are those having a total surface area in the range 150–300 $m^2/g$, a total pore volume of 3–15 $cm^3/g$ and a specified pore size distribution wherein at least 50% of the pore content is in the form of pores of diameter above 10000 Å (1000 nm) and less than 30% is in the form of pores of diameter below 1000 Å (100 nm). In contrast, in the present invention the silicas that may be employed are preferably porous high surface area silicas such as gel silicas, precipitated gel silicas and agglomerated pyrogenic silicas Accordingly the present invention provides a catalyst comprising a porous high surface area silica containing 1–10% by weight of an alkali metal (expressed as metal), wherein the catalyst contains a compound of at least one modifier element selected from boron, magnesium, aluminium, zirconium and hafnium in such amount that the catalyst contains a total of 0.25 to 2 gram atoms of said modifier element per 100 moles of silica, said modifier element compound being dispersed in the pores of said silica.

The silica employed in the invention preferably has a surface area of at least 50 $m^2g^{-1}$. The surface area may be measured by well known methods, a preferred method being a standard BET nitrogen absorption method as is well known in the art. Preferably the bulk of the surface area of the silica is present in pores of diameter in the range 5–150 nm. Preferably the bulk of the pore volume of the silica is provided by pores of diameter in the range 5–150 nm. By "the bulk" of its pore volume or surface area is provided by pores of diameter in the range 5–150 nm we mean that at least 50% of the pore volume or surface area is provided by pores of this diameter and more preferably at least 70%.

Preferred alkali metals are potassium, rubidium, or especially cesium. The alkali metal content is preferably in the range 3–8%, by weight (expressed as metal).

Gel silicas are preferred although suitable pyrogenic silicas may also be used. The preferred modifier elements are zirconium, aluminum or boron.

In an embodiment wherein boron is the modifier element the amount of boron may be from greater than 0.29 gram atoms to 2 gram atoms per 100 moles of silica.

The invention also provides a process for the manufacture of ethylenically unsaturated acids or esters thereof, particularly methacrylic acid or alkyl methacrylates, by reaction of an alkanoic acid, or ester of an alkanoic acid, of the formula R—$CH_2$—COOR', where R and R' are each, independently, hydrogen or an alkyl group, especially a lower alkyl group containing for example 1–4 carbon atoms, with formaldehyde in the presence of a catalyst as aforesaid.

The process is particularly suitable for the manufacture of methacrylic acid or especially methyl methacrylate, in which cases the alkanoic acid or ester is propionic acid or methyl propionate, respectively.

Mixtures of modifier elements may be used, for example aluminium and zirconium, or magnesium and zirconium. The total amount of the modifier element in the catalyst is preferably in the range 0.25 to 1.5 gram atoms per 100 moles of silica. Too little modifier element generally results in inadequate stabilisation of the silica support, leading to loss of activity through loss of surface area, while too much modifier element often leads to a decrease in the selectivity of the catalyst.

The catalysts may be made by impregnating silica particles of the physical dimensions required of the catalyst with a solutions of a suitable compounds, e.g. salts, of the modifier element in a suitable solvent, followed by drying. The impregnation and drying procedure may be repeated more than once in order to achieve the desired additive loading. As there appears to be competition between the modifier and alkali metal for active sites on the silica, it may be desirable for the modifier to be incorporated before the alkali metal. We have found that multiple impregnations with aqueous solutions tend to reduce the strength of the catalyst particles if the particles are fully dried between impregnations and it is therefore preferable in these cases to allow some moisture to be retained in the catalyst between successive impregnations. When using non-aqueous solutions, it may be preferable to introduce the modifier first by one or more impregnations with a suitable non-aqueous solution, e.g. a solution of an alkoxide or acetate of the modifier metal in ethanol, followed by drying and then the alkali metal may be incorporated by a similar procedure using a solution of a suitable alkali metal compound. Where aqueous solutions are employed, it is preferable to effect the impregnation using an aqueous solution of e.g. nitrates or acetates of the modifier metal and cesium of sufficient concentration that the desired loading of modifier and cesium is effected in a single step, followed by drying.

The modifier elements may be introduced into the silica particles as soluble salts but we believe that the modifier element(s) are present in the silica in the form of oxides and/or hydroxides (especially at the surface of the silica) which are formed by ion exchange during impregnation, drying, calcining or catalytic use of the catalyst.

Alternatively the modifier may be incorporated into the composition by co-gelling or co-precipitating a compound of the modifier element with the silica, or by hydrolysis of a mixture of the modifier element halide with a silicon halide. Methods of preparing mixed oxides of silica and zirconia by sol gel processing are described by Bosman et al in J Catalysis Vol 148 (1994) page 660 and by Monros et al in J Materials Science Vol 28, (1993), page 5832. Doping of silica spheres with boron during gelation from tetraethyl orthosilicate (TEOS) is described by Jubb and Bowen in J Material Science, volume 22, (1987), pages 1963–1970. Methods of preparing porous silicas are described in Iler R K, The Chemistry of Silica, (Wiley, New York, 1979), and in Brinker C J & Scherer G W "Sol-Gel Science" published by Academic Press (1990). Thus methods of preparing suitable silicas are known in the art.

The catalysts are then preferably calcined, for example in air, at a temperature in the range 300 to 600° C., particularly at 400–500° C. before use, although we have found that this may not always be necessary.

The catalysts will normally be used in the form of a fixed bed and so it is desirable that the composition is formed into shaped units, e.g. spheres, granules, pellets, aggregates, or extrudates, typically having maximum and minimum dimensions in the range 1 to 10 mm. Where an impregnation technique is employed, the silica may be so shaped prior to impregnation.

Alternatively the composition may be so shaped at any suitable stage in the production of the catalyst. The catalysts are also effective in other forms, e.g. powders or small beads and may be used in this form.

The alkanoic acid or ester thereof and formaldehyde can be fed, independently or after prior mixing, to the reactor containing the catalyst at molar ratios of acid or ester to formaldehyde of from 20:1 to 1:20 and at a temperature of 250–400° C. with a residence time of 1–100 seconds and at a pressure of 1–10 bara. Water may be present up to 60% by weight of the reaction mixture, although this is preferably minimised due to its negative effect both on catalyst decay and hydrolysis of esters to acids. Formaldehyde can be added from any suitable source. These include but are not limited to aqueous formaldehyde solutions, anhydrous formaldehyde derived from a formaldehyde drying procedure, trioxane, diether of methylene glycol and paraformaldehyde. Where forms of formaldehyde which are not as free or weakly complexed formaldehyde are used, the formaldehyde will form in situ in the synthesis reactor or in a separate reactor prior to the synthesis reactor. Thus for example, trioxane may be decomposed over an inert material or in an empty tube at temperatures over 350° C. or over an acid catalyst at over 100° C. As a second example, methylal may be decomposed by reaction with water to form formaldehyde and methanol or without water to form dimethyl ether and formaldehyde. This can be accomplished either within the reactor or in a separate reactor containing a catalyst such as an heterogeneous acid catalyst. In this case it is advantageous to feed the alkanoic acid or ester thereof ester separately to the synthesis reactor to prevent its decomposition over the acid catalyst.

When the desired product is an unsaturated ester made by reacting an ester of an alkanoic acid ester with formaldehyde, the alcohol corresponding to the ester may also be fed to the reactor either with or separately to the other components. The alcohol, amongst other effects, reduces the quantity of acids leaving the reactor. It is not necessary that the alcohol is added at the beginning of the reactor and it may for instance be added in the middle or near the back, in order to effect the conversion of acids such as propionic acid, methacrylic acid to their respective esters without depressing catalyst activity.

Other additives may be added either as inert diluents to reduce the intensity of the reaction or to control heat evolution from the catalyst as a result of reaction. Reaction modifiers may also be added, to for instance change the rate of carbon laydown on the catalyst. Thus for instance oxidising agents such as oxygen may be added at low levels to reduce the rate of coke formation. Additives may also be included to aid separations by for instance changing the composition of an azeotrope. Whilst such components to achieve the latter effect may be advantageously added after the reactor, in some circumstances it may be advantageous to include the additive in the reactor.

In order to minimise the loss of alkali metal through volatilisation, alkali metal, in a suitable form, e.g. a volatile salt, may be continuously or intermittently fed to the reactor.

The invention is illustrated by the following examples.

EXAMPLES 1–4

In these examples, the silica employed was a gel silica in the form of spheres of diameter in the range 2–4 mm having a purity of over 99%, a total surface area of about 300–350 $m^2/g$, and a pore volume of 1.04 $cm^3/g$ with 76% of the pore volume provided by pores having a diameter in the range 7–23 nm.

A series of catalysts was prepared using different modifiers by impregnating the silica with an aqueous solution of the zirconium nitrate, draining, and drying in a rotary evaporator and then in an air oven at 120° C. for 2 hours. The impregnation and drying procedure was repeated if necessary, to obtain the desired modifier content. Cesium was then incorporated by a similar procedure using an aqueous solution of cesium carbonate, to give a cesium content of about 4% by weight (expressed as metal). The catalysts were then calcined in air at 450° C. for 3 hours.

The loss of surface area by hydrolysis with time was determined by an accelerated test wherein nitrogen, containing about 40% by volume of water, was passed at a rate of 3 l/h over a 1 g sample of the catalyst at 350° C. Periodically, the surface area of the samples was determined by a nitrogen adsorption technique after purging with dry nitrogen. The results are shown in the following table:

| Example | Zr content (grams atoms per 100 moles of silica) | Surface area ($m^2/g$) after testing for (days) | | | | | |
|---|---|---|---|---|---|---|---|
| | | 0 | 2 | 5 | 9 | 12 | 18 |
| 1 (comparative) | none | 307 | 134 | 122 | 102 | 100 | 88 |
| 2 | 0.5 | 316 | 189 | 155 | — | 110 | 104* |
| 3 | 1.2 | 302 | 208 | 192 | 187 | 183 | 172 |
| 4 (comparative) | 2.5 | 307 | 240 | 221 | — | 200 | 197* |

*after 19 days testing

The catalytic performance of the catalyst samples was determined in an atmospheric pressure microreactor charged with approximately 3 g of catalyst comminuted to 1 mm size particles. Before use, the catalyst was dried at 3000° C. in a 100 ml/min stream of nitrogen for a period of 30 minutes. The catalysts were started-up at 300° C. and fed with a mixture of methyl propionate, methanol and formalin. The formalin had a formaldehyde: water: methanol weight ratio of 0.35:0.50:0.15 and the proportions of methyl propionate, methanol and formalin were such that the overall molar proportions of methyl propionate, methanol and formaldehyde were 1:1.45:0.187. The reactants were passed through the catalyst at such a rate that the contact time was initially approximately 5 seconds. After the feed had stabilised (approx. 30 mins), the catalyst temperature was increased to 350° C. and left to stabilise overnight. After approximately 16 hours of operation, the catalysts were tested for activity and selectivity by varying the feed gas flow rate. The results are shown in the following table:

| Example | Zr content * | Methyl methacrylate plus methacrylic acid - % yield (Y) or % selectivity (S) at residence time of T (sec) | | | | | | | | | | | | | | | | |
|---|---|---|---|---|---|---|---|---|---|---|---|---|---|---|---|---|---|---|
| | | T | Y | S | T | Y | S | T | Y | S | T | Y | S | T | Y | S | T | Y | S |
| 1 (comp) | none | 1.3 | 5 | 94 | 2.6 | 8 | 94 | 5.5 | 10 | 94 | 8.2 | 11 | 92 | 15.9 | 12 | 89 | | | |
| 2 | 0.5 | 1.0 | 4 | 93 | 2.0 | 7 | 96 | 5.0 | 10 | 93 | 8.0 | 11 | 93 | 15.0 | 12 | 90 | | | |
| 3 | 1.2 | 1.2 | 3 | 92 | 2.4 | 5 | 94 | 4.8 | 9 | 97 | 7.0 | 10 | 97 | 13.6 | 12 | 95 | | | |
| 4 (comp) | 2.5 | 1.1 | 3 | 93 | 2.2 | 5 | 92 | 4.6 | 8 | 90 | 6.5 | 10 | 92 | 15.6 | 11 | 88 | | | |

* gram atoms per 100 moles of silica

It is seen that zirconium gave a significant improvement in the retardation of loss of surface area and a significant improvement in selectivity at the longer residence times, except when a relatively large amount of zirconium was employed. The effect on selectivity is also demonstrated by the following table which shows the yield of "heavy" components, i.e. unwanted by products.

| Example | Zr content * | Heavies yield (%) at resident time of sec | | | | |
|---|---|---|---|---|---|---|
| | | 2 | 3 | 6 | 9 | 19 |
| 1 (comp) | none | 4 | 4 | 7 | 7 | 12 |
| 2 | 0.5 | 1 | 2 | 4 | 5 | 6 |
| 3 | 1.2 | 1 | 1 | 2 | 3 | 4 |
| 4 (comp) | 2.5 | 2 | 3 | 4 | 6 | 8 |

* gram atoms per 100 motes of silica

EXAMPLE 5–7

Catalysts were made and tested as in Examples 1 to 4 but using aluminium nitrate in place of zirconium nitrate. The results are set out in the following tables.

| Example | Al content (gram atoms per 100 moles of silica) | Surface area (m²/g) after testing for (days) | | | | | |
|---|---|---|---|---|---|---|---|
| | | 0 | 2 | 5 | 9 | 12 | 18 |
| 1 (comparative) | none | 307 | 134 | 122 | 102 | 100 | 88 |
| 5 | 0.4 | 313 | 220 | 192 | — | 160 | 154* |
| 6 | 0.7 | 325 | 180 | — | 161** | — | 123*** |
| 7 (comparative) | 2.2 | 322 | 288 | 296 | 288 | 283 | 275 |

*19 days,
**7 days,
***17 days

| Example | Al content * | Methyl methacrylate plus methacrylic acid - % yield (Y) or % selectivity (S) at residence time of T sec | | | | | | | | |
|---|---|---|---|---|---|---|---|---|---|---|
| | | T | Y | S | T | Y | S | T | Y | S |
| 1 (comparative) | none | 2.6 | 8 | 94 | 5.5 | 10 | 94 | 8.2 | 11 | 92 |
| 5 | 0.4 | 2.4 | 3 | 93 | 4.8 | 10 | 94 | 7.5 | 12 | 94 |
| 7 (comparative) | 2.0 | 3.0 | 2 | 73 | 6.3 | 3 | 75 | 9.7 | 4 | 76 |

* gram atoms per 100 moles of silica

This illustrates that aluminium is effective as a modifier to increase the stability of the silica, but the use of excessive amounts has an adverse effect upon the activity and selectivity.

EXAMPLE 8

Example 2 was repeated but using boron oxide dissolved in the cesium carbonate solution in place of zirconium nitrate to give a catalyst containing 0.8 gram atoms of boron per 100 moles of silica. The surface area was 172 m²/g after 6 days testing and thereafter fell slowly, having a value of 157 m²/g after 22 days testing. In the activity testing, at a contact time of 3.8 sec., the yield was 7% and the selectivity was 95%. At a contact time of 6.2 sec., the yield was 9% and the selectivity was 95%.

EXAMPLE 9

Example 2 was repeated but using a mixture of aluminium nitrate and hafnium oxynitrate in place of zirconium nitrate to give a catalyst containing 0.2 grams atoms of aluminium and 0.3 gram atoms of hafnium per 100 moles of silica. In the activity testing, at a contact time of 3.0 sec., the yield was 7% and the selectivity was 94%. At a contact time of 6.7 sec., the yield was 10% and the selectivity was 94%.

EXAMPLES 10–13 (COMPARATIVE)

Catalysts were made by the procedure of Example 1 using zirconia of 1 mm particle size in place of gel silica as the support. Catalysts were made with nominal cesium contents ranging from 2 to 8% by weight. The results and surface areas of the catalysts are shown in the following table:

| Ex. | Cs (%) | Surface area (m²/g) | Methyl methacrylate + methacrylic acid - % yield (Y) or % selectivity (S) at residence time of T sec | | | | | |
|---|---|---|---|---|---|---|---|---|
| | | | T | Y | S | T | Y | S |
| 10 | 2 | 93 | 2.3 | 6 | 49 | 4.7 | 6 | 44 |
| 11 | 4 | 90 | 2.4 | 4 | 38 | 5.0 | 4 | 23 |
| 12 | 6 | 74 | 2.5 | 4 | 29 | 5.4 | 3 | 15 |
| 13 | 8 | 73 | 2.1 | 2 | 27 | 4.4 | 3 | 16 |

The very poor yields and selectivities demonstrate that cesium-doped zirconia is not a suitable catalyst.

EXAMPLES 14–16

A series of catalysts were made by the procedure of Example 2, but using a mixture of zirconium nitrate and aluminium nitrate. The results of accelerated hydrolysis and activity testing are shown in the following tables.

| | Modifier * | | Surface area S (m²/g) after testing for D days | | | | | | | | | | | |
|---|---|---|---|---|---|---|---|---|---|---|---|---|---|---|
| Ex | Al | Zr | D | S | D | S | D | S | D | S | D | S | D | S |
| 3 | 0.0 | 1.2 | 0 | 302 | 2 | 208 | 5 | 192 | 9 | 187 | 12 | 183 | 18 | 172 |
| 14 | 0.2 | 0.3 | 0 | 301 | | | 6 | 190 | 9 | 183 | 14 | 163 | 19 | 149 |
| 15 | 0.2 | 0.7 | 0 | 285 | 4 | 166 | 7 | 154 | 10 | 143 | 16 | 128 | 21 | 116 |
| 16 | 0.2 | 1.0 | 0 | 308 | 2 | 234 | 5 | 215 | | | 12 | 190 | 19 | 194 |

* g atoms of modifier element per 100 moles of silica

| | Modifier * | | Methyl methacrylate plus methacrylic acid - % yield (Y) or % selectivity (S) at residence time of T sec | | | | | | | | |
|---|---|---|---|---|---|---|---|---|---|---|---|
| Ex | Al | Zr | T | Y | S | T | Y | S | T | Y | S |
| 3 | 0.0 | 1.2 | 2.0 | 5 | 96 | | | | 6.6 | 10 | 95 |
| 14 | 0.2 | 0.3 | 2.5 | 8 | 96 | 3.7 | 10 | 95 | | | |
| 15 | 0.2 | 0.7 | 2.6 | 10 | 95 | 3.8 | 12 | 94 | | | |
| 16 | 0.2 | 1.2 | 2.1 | 5 | 90 | 4.4 | 9 | 91 | | | |

* g atoms of modifier element per 100 moles of silica

EXAMPLES 17–18

To illustrate that zirconium has a surface area stabilising effect on agglomerated pyrogenic silica, pellets of 3.5 mm diameter and 4 mm length were made by impregnating pyrogenic silica having a purity of over 99%, a total surface area of about 200 m²/g, and a pore volume of 0.8 cm³/g with cesium carbonate and zirconium nitrate to give catalysts containing about 4% by weight of cesium. Surface area testing was effected as in Examples 1–4.

| | Zr | Surface area (m2/g) after testing for (days) | | | | | | |
|---|---|---|---|---|---|---|---|---|
| Example | content* | 0 | 2 | 5 | 12 | 16 | 19 | 23 |
| 17 (comp) | none | 148 | 91 | 85 | 70 | 70 | 67 | 64 |
| 18 | 0.7 | 186 | 152 | 151 | 144 | 150 | 144 | 146 |

*g atoms per 100 moles of silica

EXAMPLES 19–23

Example 18 was repeated using a pyrogenic silica of total surface area about 300 m²/g and pore volume of 0.81 cm³/g to produce catalysts containing various amounts of zirconium and about 4% by weight of cesium. The surface area and activity testing was effected as in Examples 1–4.

| | Zr | Surface area (m²/g) after testing for (days) | | | | | | |
|---|---|---|---|---|---|---|---|---|
| Example | content* | 0 | 4 | 7 | 11 | 14 | 18 | 21 |
| 19 | 0.5 | 240 | 153 | 153 | 132 | 139 | — | 136 |
| 20 | 0.7 | 249 | 169 | 161 | 167 | 149 | 155 | — |
| 21 | 0.8 | 246 | 187 | 180 | 180 | 172 | 172 | 175 |
| 22 | 1.0 | 251 | 195 | 171 | 185 | 175 | 176 | 182 |

*g atoms per 100 moles of silica

| | | Methyl methacrylate plus methacrylic acid - % yield (Y) or % selectivity (S) at residence time of T sec | | | | | | | | | | | | | | | | |
|---|---|---|---|---|---|---|---|---|---|---|---|---|---|---|---|---|---|---|
| Example | Zr content * | T | Y | S | T | Y | S | T | Y | S | T | Y | S | T | Y | S | T | Y | S |
| 19 | 0.5 | 1.0 | 3 | 89 | 2.1 | 5 | 90 | 4.4 | 8 | 93 | 7.1 | 10 | 92 | 15.4 | 11 | 89 | | | |
| 20 | 0.7 | 1.0 | 3 | 88 | 1.9 | 5 | 88 | 4.2 | 9 | 91 | 7.3 | 11 | 91 | 14.8 | 13 | 89 | | | |
| 21 | 0.8 | 1.1 | 2 | 80 | 2.3 | 5 | 81 | 4.9 | 9 | 82 | 8.6 | 11 | 83 | 20.3 | 12 | 80 | | | |
| 22 | 1.0 | 1.0 | 2 | 64 | 2.0 | 4 | 65 | 4.2 | 5 | 67 | 7.3 | 7 | 68 | 13.7 | 7 | 65 | | | |
| 23 (comp) | none | 1.2 | 4 | 94 | 2.3 | 6 | 93 | 4.3 | 8 | 95 | 7.0 | 10 | 92 | 13.3 | 11 | 90 | | | |

* g atoms per 100 moles of silica

EXAMPLES 24–26

Example 20 was repeated to give catalysts containing 0.7 gram atoms of zirconium per 100 moles of silica but using different amounts of cesium. The activity of the catalysts was assessed as in Examples 1–4.

| Example | Cs (wt %) | Methyl methacrylate plus methacrylic acid - % yield (Y) or % selectivity (S) at residence time of T sec | | | | | | | | | | |
|---|---|---|---|---|---|---|---|---|---|---|---|---|
| | | T | Y | S | T | Y | S | T | Y | S | T | Y | S |
| 24 | 2 | 1.2 | 1 | 31 | 2.2 | 2 | 38 | 4.6 | 3 | 42 | 11.1 | 4 | 45 |
| 25 | 3 | 1.1 | 2 | 73 | 2.4 | 4 | 77 | 5.0 | 7 | 79 | 11.3 | 9 | 80 |
| 20 | 4 | 1.0 | 3 | 88 | 1.9 | 5 | 88 | 4.2 | 9 | 91 | 7.3 | 11 | 91 |
| 26 | 5 | 1.1 | 4 | 89 | 2.1 | 7 | 93 | 4.2 | 9 | 90 | 10.3 | 10 | 88 |

EXAMPLES 27–33

Catalysts were prepared on the same support as in examples 1–4 but using a different method of catalyst preparation, with 4 wt % caesium and different levels of zirconium. The support was crushed and sieved to a fraction between 0.5 and 2.0 mm. Aluminium nitrate, zirconium nitrate and caesium nitrate were dissolved separately in water. The solutions were mixed and a quantity equivalent to about 1.5 times the pore volume of the support was added to the support with stirring. This was dried on a hot plate with continuous stirring. The support was then dried at 100° C. in air for 3 hours.

The loss of surface area by hydrolysis with time was determined by an accelerated test wherein nitrogen was bubbled through water at 70° C., thereby containing about 22% by volume of water on exit, and then passed at a rate of 60 l/h over a 10 g sample of catalyst at 350° C. At the beginning and the end of the tests the surface area of the samples was determined by a nitrogen adsorption method on a Micromeritics ASAP 2405 nitrogen porosimeter. The results are shown in the table below.

| Example | Zr g.atoms/100 g.moles silica | Surface Area at Start (m$^2$g$^{-1}$) | Surface Area after 14 days (m$^2$g$^{-1}$) | Fractional loss of surface area over test |
|---|---|---|---|---|
| 27 (comp) | 0.00 | 273.20 | 13.10 | 95 |
| 28 | 0.13 | 311.20 | 141.90 | 54 |
| 29 | 0.26 | 304.40 | 189.00 | 38 |
| 30 | 0.39 | 303.20 | 206.90 | 32 |
| 31 | 0.49 | 303.90 | 243.80 | 20 |
| 32 | 0.66 | 313.00 | 228.40 | 27 |
| 33 | 1.31 | 311.00 | 299.00 | 4 |

The catalytic performance of the catalysts was tested in a pressurised microreactor charged with approximately 1 g of catalyst. Catalysts were heated to 300° C. for 1 hour in a flow of nitrogen before the reactants-containing stream was introduced in a flow of 25 vol % of a mixture of molar composition methyl propionate: formaldehyde: methanol: water of 1:1:0.19:0.048 and 75 vol % nitrogen at 4 bar absolute, such that the total partial pressure of organics and water was 1 bar absolute. The contact time was adjusted to give about 10% yield where possible. Performances were measured after 18 hours on stream. The results are shown in the table below and show that catalyst stability towards hydrothermal sintering increases continuously with zirconium content. Catalyst performance is reasonably consistent up to about 0.5 g atoms zirconium/100 g.moles silica and declines thereafter. These results indicate an optimum performance combining these two effects at 0.35 to 0.5 g atoms zirconium/100 g.moles silica. Comparison with examples 2–4 shows that the optimum level is dependent on the method of catalyst preparation.

| Example | Zr (g.atoms/100 g.moles silica) | Contact Time (s) | Yield of MMA + MAA | Selectivity to MMA + MAA |
|---|---|---|---|---|
| 27 (comp) | 0.00 | 1.83 | 10.30 | 94.06 |
| 28 | 0.13 | 1.54 | 10.03 | 93.36 |
| 29 | 0.26 | 2.63 | 12.86 | 93.81 |
| 30 | 0.39 | 1.64 | 7.45 | 93.79 |
| 31 | 0.49 | 3.02 | 10.00 | 94.14 |
| 32 | 0.66 | 2.16 | 10.78 | 89.84 |
| 33 | 1.31 | 38.82 | 3.20 | 75.84 |

EXAMPLES 34–38

Catalysts were prepared on crystalline zirconia powder (surface area 38 m$^2$g$^{-1}$) to which caesium nitrate was added by the method described in Example 28. Catalysts were tested for activity using the method of Example 27. The results are shown in the table below and show that zirconia alone is not a suitable support for MMA synthesis. The best result at 2 wt % caesium was not sustained and after 24 hours running fell to 60% selectivity. Levels of diethyl ketone (DEK), an unwanted by-product of the reaction, are also very high except for the most favourable loading of caesium. DEK is a particular problem at such levels because it has a boiling point which is very close to that of MMA and so it cannot be removed by distillation.

| Example | Cs (wt %) | Contact Time (s) | Yield of MMA + MAA | Selectivity to MMA + MAA | DEK yield (% of MMA + MAA) |
|---|---|---|---|---|---|
| 34 | 0 | 10.00 | 3.09 | 7.75 | 32.00 |
| 35 | 2 | 3.00 | 9.50 | 74.80 | 0.07 |
| 36 | 4 | 3.00 | 1.38 | 2.11 | 41.00 |
| 37 | 6 | 52.10 | 3.04 | 15.64 | 27.00 |
| 38 | 8 | 118.60 | 1.57 | 2.65 | 41.00 |

EXAMPLES 39–43 (COMPARATIVE)

Catalysts were prepared by physically mixing the pure silica support used in Examples 1–4 ground to 0.6–1.0 mm mesh size with portions of the zirconia powder used in Examples 34–38 in various proportions. The mixed support was then impregnated with caesium nitrate using the method described in Examples 27–33 to give 4 wt % caesium based on weight of silica plus zirconia. The results of catalytic testing and for stability towards hydrothermal sintering using the methods of Examples 27–33 are shown in the table below:

| Example | Zr content (gatom/100 gmol SiO$_2$) | contact time (sec) | Yield of MMA + MAA (%) | selectivity to MMA + MAA (%) | surface area at Start (m$^2$g$^{-1}$) | surface area after 14 days (m$^2$g$^{-1}$) | Fractional loss of surface area over test (%) |
|---|---|---|---|---|---|---|---|
| 39(comp) | 0.00 | 1.83 | 10.30 | 94.06 | 273.2 | 13.1 | 95 |
| 40(comp) | 0.11 | 1.90 | 10.46 | 90.78 | 304.8 | 128.3 | 58 |
| 41(comp) | 0.45 | 1.30 | 11.11 | 92.74 | 298.2 | 133.3 | 55 |
| 42(comp) | 2.24 | 1.30 | 10.97 | 91.50 | 299.3 | 132.5 | 56 |
| 43(comp) | 4.48 | 2.40 | 10.51 | 93.96 | 269.4 | 121.4 | 55 |

The results show that the presence of zirconium in the form of a physical mixture of zirconia with silica has some beneficial effect upon the loss of surface area after exposure to water and that this effect does not appear to depend upon the amount of zirconia present in the mixture. Zirconium in this form is not, however, as effective as when Zirconium is incorporated into the silica by dispersion from solution as demonstrated by Examples 29–31. In addition the yield of DEK was considerably greater using the catalysts formed from 8 mixture of silica and zirconia as shown in the following table:

| Example | DEK yield on MMA + MAA (%) |
|---|---|
| 40(comp) | 0.15 |
| 41(comp) | 0.3 |
| 42(comp) | 0.2 |
| 43(comp) | 0.14 |
| 29 | 0.02 |
| 30 | 0.02 |
| 31 | 0.01 |

EXAMPLES 44–48

Catalysts were prepared by the method used in Example 28 except the boron oxide was used instead of zirconium nitrate. The catalysts were tested for catalytic performance and stability towards hydrothemal sintering using the method described in that Example and the results are shown below. The beneficial effect of boron on sintering is observed, together with the adverse impact on catalyst performance commencing at above 2 g. atom/100 g atom of silica.

| Example | B (g.atom/100 g.atom SiO2) | contact Time (sec) | Yield of MMA + MAA (%) | Selectivity to MMA + MAA (%) | Surface area at start (m$^2$g$^{-1}$) | Surface Area after 14 days (m$^2$g$^{-1}$) | Fractional loss of surface area over test (%) |
|---|---|---|---|---|---|---|---|
| 27 (comp) | 0.00 | 1.83 | 10.30 | 94.06 | 273.20 | 13.10 | 95.20 |

| Example | B (g.atom/100 g.atom SiO2) | contact Time (sec) | Yield of MMA + MAA (%) | Selectivity to MMA + MAA (%) | Surface area at start (m²g⁻¹) | Surface Area after 14 days (m²g⁻¹) | Fractional loss of surface area over test (%) |
|---|---|---|---|---|---|---|---|
| 44 | 0.39 | 1.66 | 9.50 | 93.59 | 311.30 | 99.60 | 68.80 |
| 45 | 0.78 | 5.33 | 9.97 | 93.88 | | | |
| 46 | 1.16 | 3.02 | 11.13 | 94.41 | | | |
| 47 | 2.00 | 3.88 | 11.61 | 92.05 | | | |
| 48 | 3.90 | 5.36 | 7.48 | 91.19 | | | |

EXAMPLE 49

A catalyst was prepared by the method in Example 28 but using 0.39 g atom hafnium instead of 0.39 g atom zirconium. hafnium oxynitrate being used instead of zirconium nitrate. The catalyst was tested for stability towards hydrothermal sintering for catalytic activity by the method used in Example 27–33. The surface area fell from 309 m²g⁻¹ to 125 m²g⁻¹ over the test. At 1.9 second contact time the yield of methyl methacrylate plus methacrylic acid was 10.33% and selectivity was 92.5%.

EXAMPLE 50

Catalysts containing caesium and zirconium were prepared on a high purity gel silica in the form of spheres of diameter in the range 2–4 mm having a purity of over 99%, a surface area of 127 m²g⁻¹ by the methods described in Example 28.

EXAMPLE 51–54

Catalysts containing caesium and zirconium were prepared on high purity gel silicas in the form of powders with surface areas as indicated in the table below.

EXAMPLE 55–58

Catalysts containing caesium and zirconium were prepared on a pyrogenic silica powder with compositions as indicated in the table below.

| Example | wt % Cs | gatom Zr/100 gatom SiO₂ | Starting surface area (m²g⁻¹) | Surface area after 14 days (m²g⁻¹) | % of surface area lost in test |
|---|---|---|---|---|---|
| 50 | 4 | 0.39 | 127.30 | 105.40 | 17 |
| 51(comp) | 6 | — | 281.70 | 113.20 | 60 |
| 52 | 6 | 0.39 | 271.70 | 174.30 | 36 |
| 53(comp) | 6 | — | 208.00 | 103.80 | 50 |
| 54 | 6 | 0.39 | 215.20 | 163.40 | 24 |
| 55(comp) | 4 | — | 226.70 | 76.90 | 66 |
| 56 | 4 | 0.39 | 264.40 | 132.40 | 50 |
| 57(comp) | 6 | — | 225.60 | 59.10 | 74 |
| 58 | 6 | 0.39 | 209.90 | 66.20 | 68 |

Comparison of samples without and with zirconium shows that the improvement in retention of surface area is obtained for all the supports examined.

EXAMPLES 59–63

Catalysts were prepared using acetate salts instead of nitrate, on the same support as in Examples 1–4. The support was crushed and sieved to a fraction between 0.5 and 2.0 mm. Aluminium hydroxide and caesium hydroxide were dissolved separately in 5% and 10% aqueous acetic acid. A 15% solution of zirconium acetate in aqueous acetic acid (ex Aldrich) was used as received. The solutions were mixed and a quantity equivalent to about 1.5 times the pore volume of the support was added to the support with stirring. This was dried on a hot plate with continuous stirring before being dried for 2 hours at 110° C. Catalyst formulations are shown in the table below:

| Example | Cs wt % | Zr (g atom/100 gatom of silicon) | Al (g atom/100 gatom of silicon) |
|---|---|---|---|
| 59 | 5 | 0.33 | 0.22 |
| 60 | 5 | 0.66 | 0 |
| 61 | 5 | 0.5 | 0 |
| 62 | 5 | 0.33 | 0.44 |

The catalysts were tested for initial performance and hydrothermal stability by the method described in examples 1–4. The results are shown in the two tables below.

| Methyl methacrylate plus methacrylic acid - % yield (Y) or % selectivity (S) at residence time of T sec | | | | | | | | | | | | | | | |
|---|---|---|---|---|---|---|---|---|---|---|---|---|---|---|---|
| Example | T | Y | S | T | Y | S | T | Y | S | T | Y | S | T | Y | S |
| 59 | 1.1 | 5.1 | 94.8 | 2.2 | 7.5 | 95.7 | 2.9 | 8.8 | 95.4 | 5.7 | 11.2 | 94.3 | 8.6 | 12.8 | 92.0 |
| 60 | 0.3 | 5.1 | 84.6 | 2.6 | 7.4 | 86.3 | 3.6 | 9.0 | 86.6 | 6.1 | 10.8 | 86.5 | 10.4 | 11.6 | 85.8 |

-continued

| | Methyl methacrylate plus methacrylic acid - % yield (Y) or % selectivity (S) at residence time of T sec | | | | | | | | | | | | | | |
|---|---|---|---|---|---|---|---|---|---|---|---|---|---|---|---|
| Example | T | Y | S | T | Y | S | T | Y | S | T | Y | S | T | Y | S |
| 61 | 1.2 | 5.5 | 91.1 | 2.4 | 8.0 | 91.5 | 3.3 | 9.7 | 91.4 | 5.5 | 11.4 | 90.5 | 9.5 | 12.5 | 87.4 |
| 62 | 1.1 | 5.1 | 95.0 | 2.3 | 7.4 | 95.3 | 3.3 | 9.0 | 95.1 | 5.5 | 10.9 | 94.4 | 8.8 | 12.5 | 92.5 |

| | Surface area after n days on line (m²g-1) Days on Line | | | |
|---|---|---|---|---|
| Example | 0 | 7 | 14 | 28 |
| 59 | 309 | 165 | 112 | 99 |
| 60 | 296 | 167 | 169 | 158 |
| 61 | 296 | 142 | 119 | 103 |
| 62 | 309 | 159 | 132 | 128 |

Thus, these catalysts display satisfactory catalytic performance and enhanced stability towards sintering of silica compared to Example 1.

The invention claimed is:

1. A process for the manufacture of ethylenically unsaturated acids or esters thereof comprising reacting an alkanoic acid or an ester of an alkanoic acid of the formula R¹—CH₂—COOR, where R and R¹ are each, independently, hydrogen, or an alkyl group, with formaldehyde in the presence of a catalyst, wherein the catalyst comprises a porous high surface area silica containing 1–10% by weight of an alkali metal (expressed as metal), wherein the catalyst contains a compound of at least one modifier element selected from magnesium, aluminium, zirconium and/or hafnium in such amount that the catalyst contains a total of 0.25 to 2 gram atoms of said modifier element per 100 moles of silica, and said modifier element compound being dispersed in the pores of said silica.

2. A process according to claim 1, wherein the ester of an alkanoic acid is methyl propionate which is reacted with formaldehyde in the presence of methanol.

3. A process according to claim 2, wherein formaldehyde is supplied in the form of formalin.

4. A process for manufacturing methyl methacrylate comprising reacting methyl propionate with formaldehyde and methanol in the presence of a catalyst comprising a porous high surface area silica containing 1–10% by weight of cesium, expressed as metal, wherein the catalyst contains a zirconium compound in such amount that the catalyst contains a total of 0.25 to 0.5 gram atoms of zirconium per 100 moles of silica, said zirconium compound being dispersed in the pores of said silica.

5. A process for the manufacture of ethylenically unsaturated acids or esters thereof by reaction of an alkanoic acid, or ester of an alkanoic acid, of the formula

R'—CH₂—COOR, where R and R' are each, independently, hydrogen or an alkyl group, with formaldehyde in the presence of a catalyst comprising a porous high surface area silica containing 1–10% by weight of an alkali metal (expressed as metal), wherein the catalyst contains a compound of at least one modifier element selected from the group consisting of boron, magnesium, aluminum, zirconium and hafnium, in such amount that the catalyst contains a total of 0.25 to 2 gram atoms of said modifier per 100 moles of silica, said modifier element compound being dispersed in the pores of said silica.

6. A process according to claim 5, wherein the ester of the alkanoic acid is methyl propionate and is reacted with formaldehyde in the presence of methanol.

7. A process according to claim 6, wherein the formaldehyde is supplied in the form of formalin.

8. A process according to claim 5, wherein the formaldehyde is supplied in the form of formalin.

9. A process according to claim 1, wherein the formaldehyde is supplied in the form of formalin.

10. A process for manufacturing methyl methacrylate comprising reacting methyl propionate with formaldehyde and methanol in the presence of a catalyst comprising a porous high surface area silica containing 1–10% by weight of cesium (expressed as metal), wherein the catalyst contains a zirconium compound in such amount that the catalyst contains a total of 0.25 to 2 gram atoms of zirconium per 100 moles of silica, said zirconium compound being dispersed in the pores of said silica.

* * * * *